(12) United States Patent
Jeevanandam et al.

(10) Patent No.: US 11,135,420 B2
(45) Date of Patent: Oct. 5, 2021

(54) INTRODUCER ASSEMBLY AND METHOD OF USE THEREOF

(71) Applicant: NuPulseCV, Inc., Raleigh, NC (US)

(72) Inventors: Valluvan Jeevanandam, Raleigh, NC (US); Robert Smith, Raleigh, NC (US)

(73) Assignee: NuPulseCV, Inc., Raleigh, NC (US)

( * ) Notice: Subject to any disclaimer, the term of this patent is extended or adjusted under 35 U.S.C. 154(b) by 107 days.

(21) Appl. No.: 16/693,821

(22) Filed: Nov. 25, 2019

(65) Prior Publication Data

US 2020/0086021 A1 Mar. 19, 2020

Related U.S. Application Data

(62) Division of application No. 15/423,375, filed on Feb. 2, 2017, now Pat. No. 10,518,009.

(60) Provisional application No. 62/290,866, filed on Feb. 3, 2016.

(51) Int. Cl.
| | | |
|---|---|---|
| *A61M 1/12* | (2006.01) | |
| *A61M 60/40* | (2021.01) | |
| *A61M 60/135* | (2021.01) | |
| *A61M 60/148* | (2021.01) | |
| *A61M 60/857* | (2021.01) | |
| *A61M 25/09* | (2006.01) | |

(52) U.S. Cl.
CPC ............ *A61M 60/40* (2021.01); *A61M 25/09* (2013.01); *A61M 60/135* (2021.01); *A61M 60/148* (2021.01); *A61M 60/857* (2021.01); *A61M 2205/15* (2013.01); *A61M 2205/32* (2013.01); *A61M 2205/3344* (2013.01); *A61M 2205/3523* (2013.01)

(58) Field of Classification Search
USPC ......................................................... 600/18
See application file for complete search history.

(56) References Cited

U.S. PATENT DOCUMENTS

| | | | |
|---|---|---|---|
| 4,531,512 | A | 7/1985 | Wolvek |
| 5,161,534 | A | 11/1992 | Berthiaume |
| 5,201,707 | A | 4/1993 | Kanai |
| 5,230,692 | A | 7/1993 | Kanai |
| 5,454,788 | A | 10/1995 | Walker |
| 7,374,531 | B1 | 5/2008 | Kantrowitz |
| 2001/0016725 | A1 | 8/2001 | Valley |
| 2003/0032974 | A1 | 2/2003 | Leschinsky |
| 2003/0171642 | A1 | 9/2003 | Schock |
| 2003/0229295 | A1 | 12/2003 | Houde |

(Continued)

FOREIGN PATENT DOCUMENTS

| | | |
|---|---|---|
| CN | 102958552 | 3/2013 |
| CN | 103002929 A | 3/2013 |
| CN | 105188797 A | 12/2015 |

(Continued)

OTHER PUBLICATIONS

Chinese Office Action (with English translation) for App. No. CN201780009271.5, dated Jan. 29, 2021, 11 pages.

(Continued)

*Primary Examiner* — Nicole F Lavert
(74) *Attorney, Agent, or Firm* — Loeb & Loeb LLP (57) ABSTRACT

The invention provides an introducer assembly for delivering a blood pump into vasculature of a subject, as well as a method for utilizing the assembly.

20 Claims, 10 Drawing Sheets

(56) References Cited

U.S. PATENT DOCUMENTS

2004/0236170 A1* 11/2004 Kim .................... A61B 17/11
                                                              600/16
2008/0312671 A1    12/2008 Riles

FOREIGN PATENT DOCUMENTS

| EP | 1982742 A2 | 10/2008 |
| JP | H724060 A | 1/1995 |
| JP | H0951954 | 2/1997 |
| JP | 2013508094 A | 3/2013 |
| JP | 2014147584 A | 8/2014 |
| WO | 0113976 A1 | 3/2001 |
| WO | 2011050279 | 4/2011 |

OTHER PUBLICATIONS

Japanese Office Action (including English translation) for App. No. JP2018-540454, dated Feb. 19, 2021, 12 pages.
International Search Report dated Apr. 17, 2017, regarding PCT/US2017/016196. 2 pages.

* cited by examiner

INTRODUCER ASSEMBLY AND METHOD OF USE THEREOF

CROSS-REFERENCE TO RELATED APPLICATIONS

This application is a divisional application of U.S. patent application Ser. No. 15/423,375, now U.S. Pat. No. 10,518,009, filed Feb. 2, 2017, which claims the benefit of of U.S. Provisional Patent Application Ser. No. 62/290,866, filed Feb. 3, 2016, the entire contents of which are incorporated herein by reference.

TECHNICAL FIELD

The invention relates generally to a cardiac assist device (CAD) and more particularly to a delivery tool, and a method of using the delivery tool for implanting and positioning a blood pump assembly of the CAD within a subject.

BACKGROUND

The use of CADs is a well known method for treating heart failure. A blood pump (i.e., a balloon) is positioned inside the aorta, typically in the proximal descending aorta. The pump typically comprises a displacement volume of 40-50 cc, and works in series with the heart to augment blood flow. During diastole, the pump is inflated, thereby driving blood in the ascending aorta and aortic arch into the coronary arteries to supply oxygen to the heart muscle. During systole, as the left ventricle contracts, the pump is deflated so as to decrease the afterload.

While the use and implantation of the blood pump portion of a CAD is well known, conventional methods of implantation may lead to infection as well as a risk of other complications. There exists a need for a blood pump delivery tool and method of delivering a blood pump into the vasculature of a subject which provides convenience as well as reduced risk of complications.

SUMMARY

The invention provides an introducer assembly for delivering a blood pump into the vasculature of a subject, as well as a method for utilizing the assembly.

Accordingly, in one aspect, the invention provides an introducer assembly for introducing a blood pump. The assembly includes: a) a shaft elongated along a longitudinal axis, the shaft having a distal end, a proximal end, a lumen extending along the longitudinal axis from the distal end to the proximal end, and a collet mechanism disposed at the proximal end for receiving a guidewire; and b) a locking component having a distal end and a proximal end, the locking component adapted such that the distal end of the locking component reversibly couples to the proximal end of the shaft. The locking component has a locked configuration and an unlocked configuration such that when in the locked configuration, a gripping force is created between the collet mechanism and the guidewire.

In another aspect, the invention provides a method of introducing a blood pump into a blood vessel of a subject utilizing an introducer assembly of the invention. The method includes providing an introducer assembly for introducing the blood pump, elongating the inflatable balloon by advancing a guidewire distally along the lumen of the introducer shaft through the collet mechanism and toward the distal end of the balloon when the locking component is in an unlocked configuration, transitioning the locking component to the locked configuration such that the guidewire is slidably immovable within the collet, advancing the balloon into and along a length of vasculature, such as a blood vessel, transitioning the locking component to the unlocked configuration, withdrawing the guidewire, and disconnecting the distal end of the shaft from a drive line of the blood pump. In embodiments, a vacuum force may be applied to the inflatable balloon after the locking component is transitioned to the locked configuration. In one embodiment, the balloon is advanced through an access port of an arterial interface device (AID) of the CAD system which provides access to the blood vessel. In a related embodiment, a sheath is applied over the introducer assembly and the access port before advancing the balloon into the blood vessel.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION

U.S. patent application Ser. Nos. 14/659,375 and 14/476,656, and U.S. Pat. Nos. 8,323,174 and 7,892,162 are incorporated herein in their entireties. The components, devices, modules, source code, and the like, associated with the CAD and components thereof as disclosed in U.S. patent application Ser. Nos. 14/659,375 and 14/476,656, and U.S. Pat. Nos. 8,323,174 and 7,892,162 are also disposed in the CAD and components thereof as described herein. In addition, the functions and methods disclosed in U.S. patent application Ser. Nos. 14/659,375 and 14/476,656, and U.S. Pat. Nos. 8,323,174 and 7,892,162, that utilize those components, devices, modules, source code, and the like, are also operative using the CAD described herein.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

While the introducer assembly of the present invention is generally disclosed with use of a CAD of the disclosure, it may be utilized with a variety of devices and in a variety of procedures which involve vascular implantation of a blood pump device.

Figure 1:
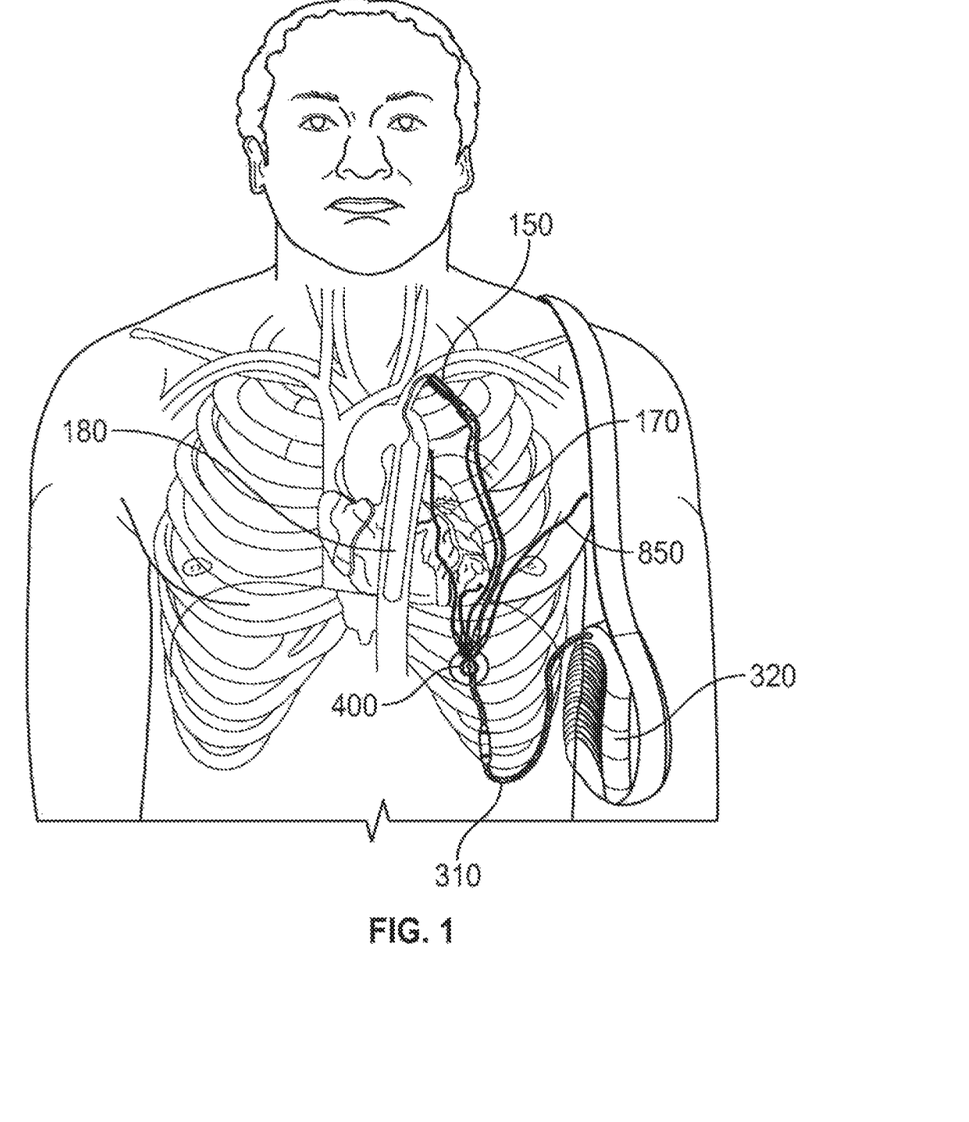
FIG. 1 schematically shows a CAD, also referred to herein as an intravascular Ventricular Assist System (iVAS), including blood pump 180, internal drive line 170, arterial interface device (AID) 150, skin interface device (SID) 400, external drive line 310, external driver 320, and subcutaneous ECG leads 850 superimposed on a human thorax.

In a primary embodiment, the CAD of the disclosure, also referred to herein as an iVAS, operates on the principle of counterpulsation similar to an intra-aortic balloon pump (IABP). Components of the system are shown in FIG. 1. During diastole, inflation of blood pump 180 augments the native heart's cardiac output by displacing blood in the aorta, pushing it downstream. At the start of systole (peak of the R-wave), the blood pump 180 deflates, decreasing aortic pressure and reducing the work required of the left ventricle during subsequent ejection. Counterpulsation has been a standard treatment for cardiogenic shock for decades, providing circulatory support for hours to weeks.

In various embodiments, implantation of an iVAS requires implanting four components: AID 150, blood pump 180, SID 400, and internal drive line 170. To facilitate implantation, custom tools and methodology were developed, including the introducer assembly of the present invention.

Figure 2:
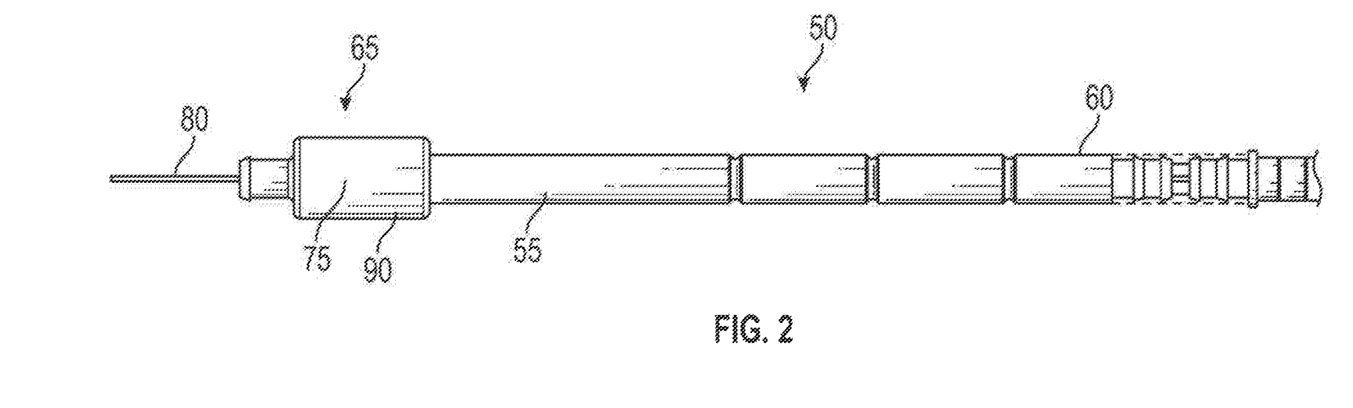
FIG. 2 schematically shows an introducer assembly 50 for use with implanting a blood pump of a CAD in a patient.
Figure 3:
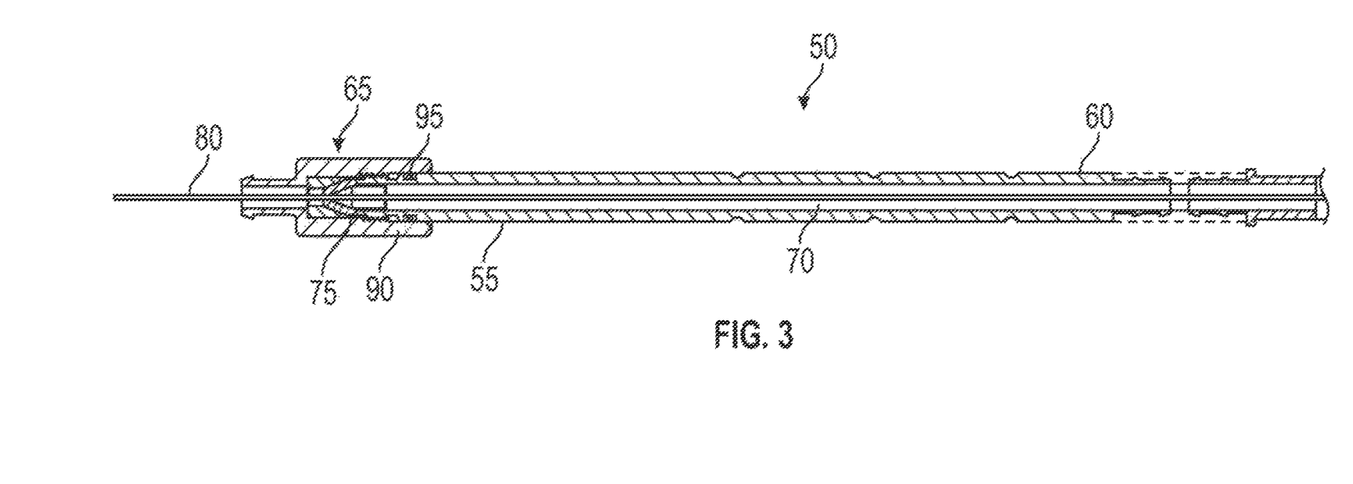
FIG. 3 is a cross-sectional view of the introducer assembly of FIG. 2.
Figure 4:
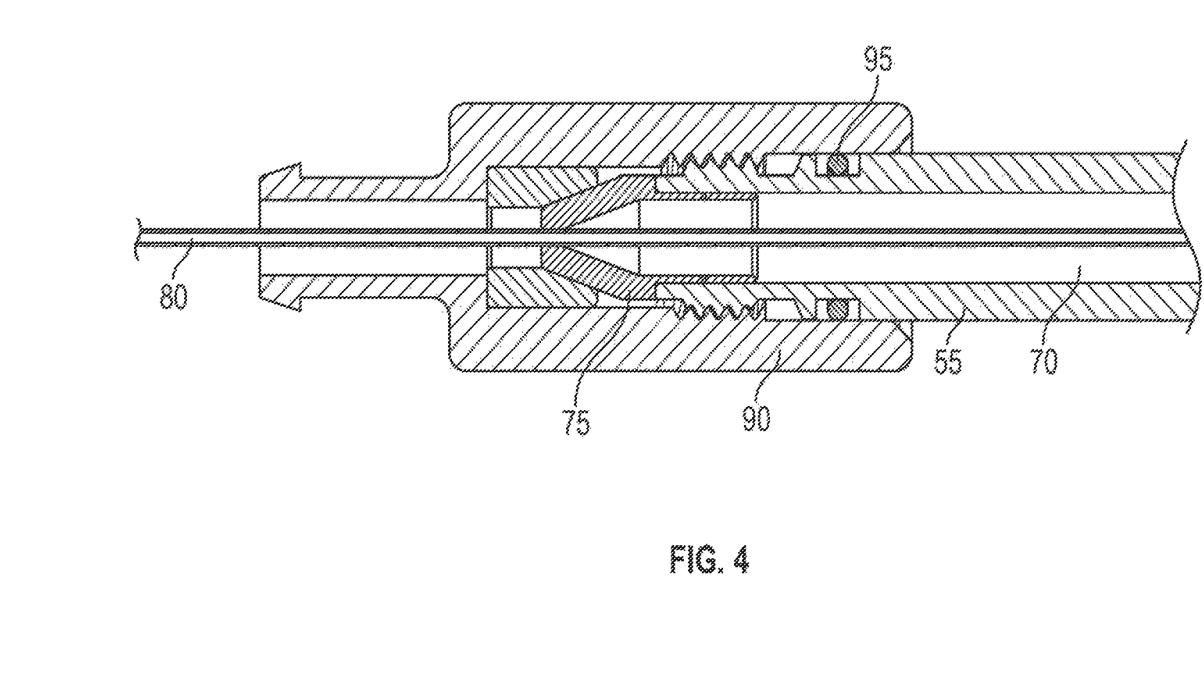
FIG. 4 is an expanded cross-sectional view of locking component 90 and associated collet mechanism 75 of the introducer assembly of FIGS. 2 and 3.

Accordingly, in one aspect, the invention provides an introducer assembly for introducing a blood pump. With reference to FIGS. 2-4, the assembly 50 includes: a) a shaft 55 elongated along a longitudinal axis, the shaft having a distal end 60, a proximal end 65, a lumen 70 extending along the longitudinal axis from the distal end 60 to the proximal end 65, and a collet mechanism 75 disposed at the proximal end 65 for receiving a guidewire 80; and b) a locking component 90 having a distal end and a proximal end, the locking component adapted such that the distal end of the locking component reversibly couples to the proximal end of the shaft. The locking component has a locked configuration and an unlocked configuration such that when in the locked configuration, a gripping force is created between the collet mechanism 75 and a guidewire 80 inserted within lumen 70.

Notably, the proximal end 65 of the shaft is adapted to form a fluid tight seal with the locking component 90. This can be accomplished by inclusion of o-ring 95. The fluid tight seal prevents blood loss during introduction of the blood pump 180 into the vasculature. The o-ring 95 also creates an air tight seal between the introducer and the blood pump 180 allowing the blood pump to be deflated during insertion into the vasculature.

Figure 6A:
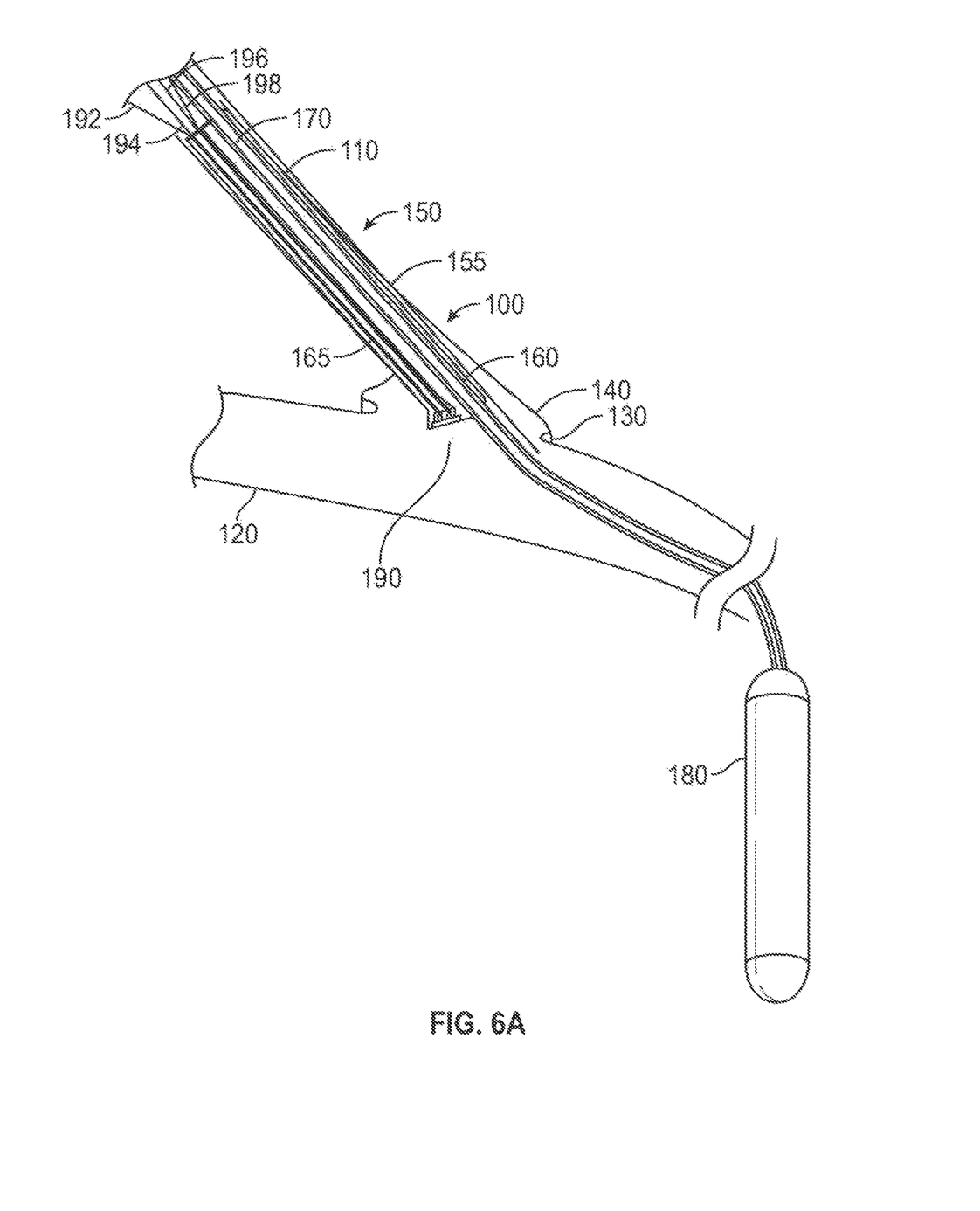
FIG. 6A schematically shows portions of a CAD implanted in a patient using AID 150.
Figure 6B:
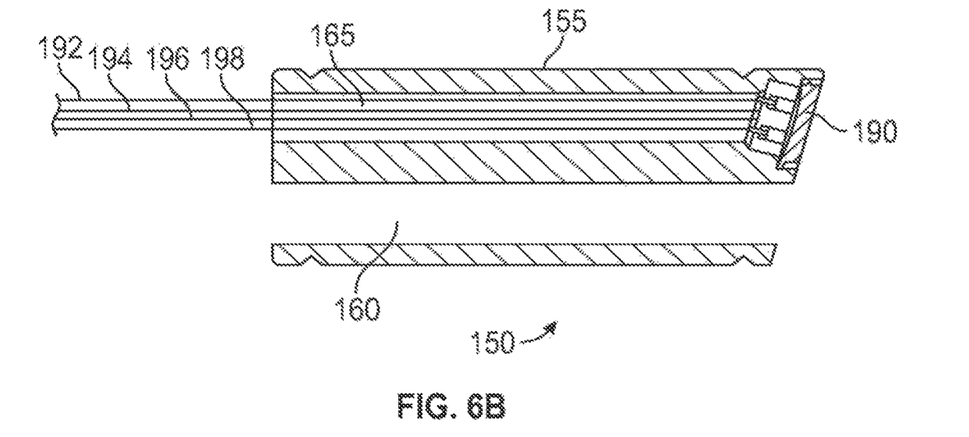
FIG. 6B is a cross-sectional view of AID 150 of FIG. 6A.

FIGS. 6A and 6B illustrate an AID 150 of the iVAS of the disclosure. Referring to FIG. 6A, a vascular interface 100 is formed using a vascular graft 110 attached to an artery 120 with a suture ring 130 at the position of an incision in the artery. The particular graft shown flares at its distal end 140. AID 150 sits inside the graft 110, filling the interior of the graft 110.

Sewing the suture ring 130 to the subclavian artery is the first task the surgeon performs when implanting the system. Next, graft 110 is sutured to the suture ring 130.

With reference to FIGS. 6A and 6B, AID 150 comprises a body 155. In certain embodiments, body 155 comprises a polyurethane. In certain embodiments, body 155 comprises a polysiloxane. In the illustrated embodiment of FIGS. 1A and 1B, body 155 is formed to include two lumens extending therethrough. Lumen 160 is utilized to pass internal drive line 170 through AID 150.

Figure 7A:
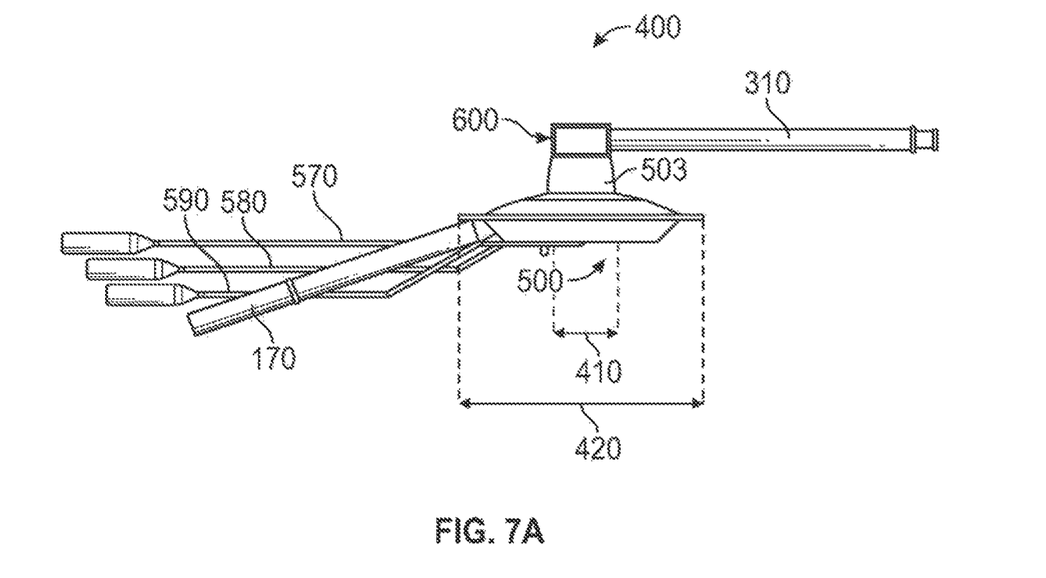
FIG. 7A illustrates SID 400 comprising implantable base 500 and SID cap 600.
Figure 7B:
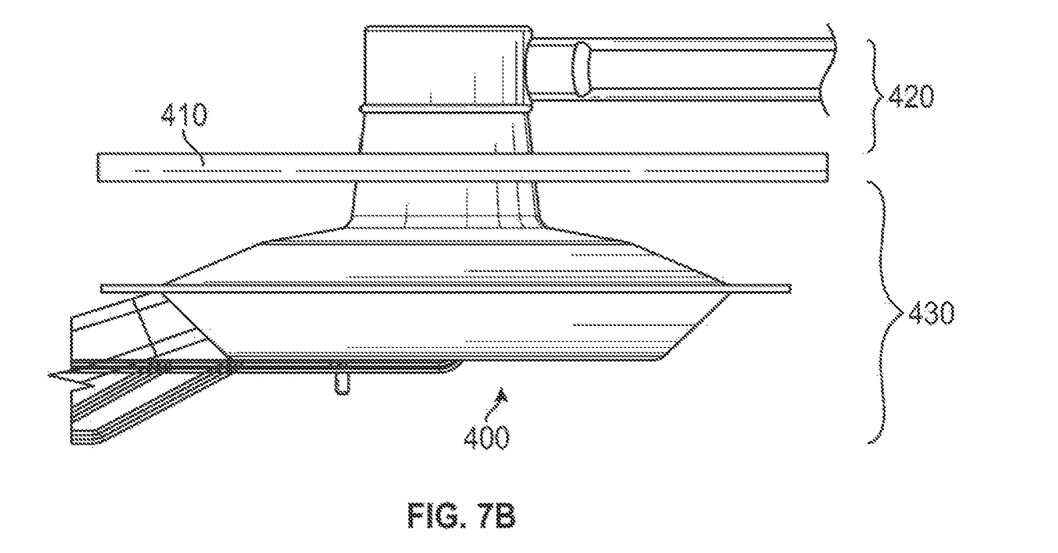
FIG. 7B illustrates a supracutaneous portion 420 and a subcutaneous portion 430 of the SID 400 of FIG. 7A when disposed within a patient.

The second lumen 165 houses a pressure sensor 190 to measure arterial pressure, and sensor leads 192, 194, 196, and 198, to interconnect sensor 190 to SID 400 (FIGS. 7A and 7B). Sensor leads 192, 194, 196, and 198, are used to provide power to sensor 190, provide a ground connection, to provide clock signals to sensor 190, and to communication arterial pressure signals from sensor 190 to SID 400.

Lumen 160 which extends through the length of the AID 150 is filled by the internal drive line 170. Internal drive line 170 in turn is connected at its distal end to a pump 180. In certain embodiments, inflation catheter is formed to have an inner diameter in the range 3 to 6 mm (often about 5 mm), although other diameters are possible as well.

Not shown in FIG. 6A is the proximal end of the drive line 170. Because the pump 180 needs to inflate and deflate in coordination with the cardiac cycle in order to function as a ventricular assist device, the blood pump 180 must be in fluid communication with a driver (e.g., an air compressor or pump) via drive line 170.

In embodiments wherein such a driver is external to the body as shown in FIG. 1, the SID 400 (FIGS. 7A and 7B) allows the design of the system to be composed of parts both implanted and external to the patient's body. The drive line 170 is attached to SID 400, and SID 400 is attached to the fluid driver. In certain embodiments, the driver 320, the drive line 170 and the pump 180 form a closed air system, wherein that closed system includes a well-defined and precisely controlled volume of air. Such a well-defined and precisely-controlled volume of air facilitates leak detection.

In certain embodiments, air volume and movement of air is precisely controlled using, for example and without limitation, a bellows driven by one or more linear actuators. In descriptions of the skin interface device herein, the drive line 170 is alternatively referred to as an internal drive line.

Figure 8:
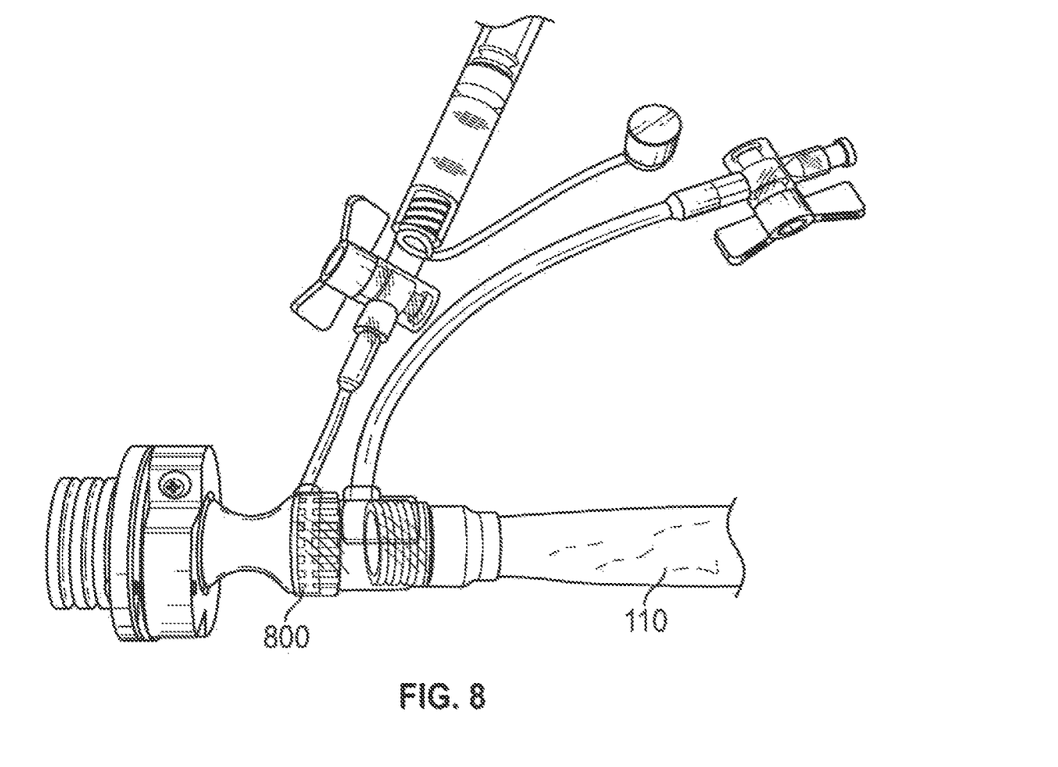
FIG. 8 shows an access port assembly 800 used to occlude vascular graft 110 during implantation of a blood pump.
Figure 9:
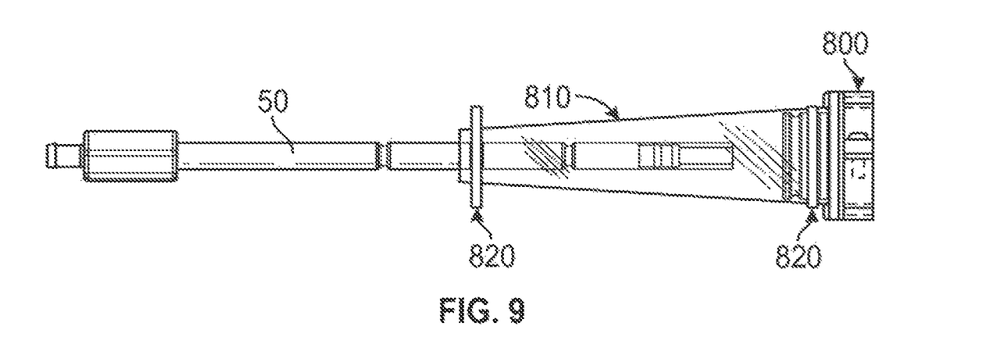
FIG. 9 shows an assembly of introducer assembly 50 in combination with an access port assembly 800 and optional sheath 810 during implantation of a blood pump with optional sutures 820 being disposed on opposing openings of the sheath 810.

With reference to FIGS. 8 and 9, in implantation of the blood pump 180, once the anastomosis of the suture ring 130 and graft 110 is complete as discussed above, an access port assembly 800 containing an iris valve (FIG. 8) is inserted into graft 110 at its proximal end creating hemostasis. The surgeon then optionally attaches a sheath 810 (FIG. 9) to the proximal end of the access port assembly 800. Inside the sheath 810 is the blood pump 180 in its deflated state. The other end of the sheath 810 is tied off to the shaft of the introducer assembly 50 as illustrated in FIG. 9. The sheath 810 is attached to the access port assembly 800 and shaft of the introducer assembly 50 via sutures 820. The function of the access port is to minimize blood loss during pump insertion. The sheath is used to collect any blood that escapes through the access port. The blood pump 180 is then implanted in the patient's vasculature, i.e., the descending thoracic aorta. To implant the pump, the surgeon inserts and guides it down the patient's subclavian artery, traverses the subclavian aorta bifurcation, and then travels down the aorta to the final location. The pump does not have the mechanical rigidity to permit implantation without the introducer 50.

In embodiments, the sheath is not required in implantation. In such embodiments, in implantation of the blood pump 180, once the anastomosis of the suture ring 130 and graft 110 is complete as discussed above, an access port assembly 800 containing an iris valve (FIG. 8) is inserted into graft 110 at its proximal end creating hemostasis. The sheath is not required since graft 110 may be reversibly clamped to prevent blood loss. The blood pump 180 is then implanted in the patient's vasculature, i.e., the descending thoracic aorta. To implant the pump, the surgeon inserts and guides it down the patient's subclavian artery, traverses the subclavian aorta bifurcation, and then travels down the aorta to the final location. The pump does not have the mechanical rigidity to permit implantation without the introducer 50.

Figure 5:
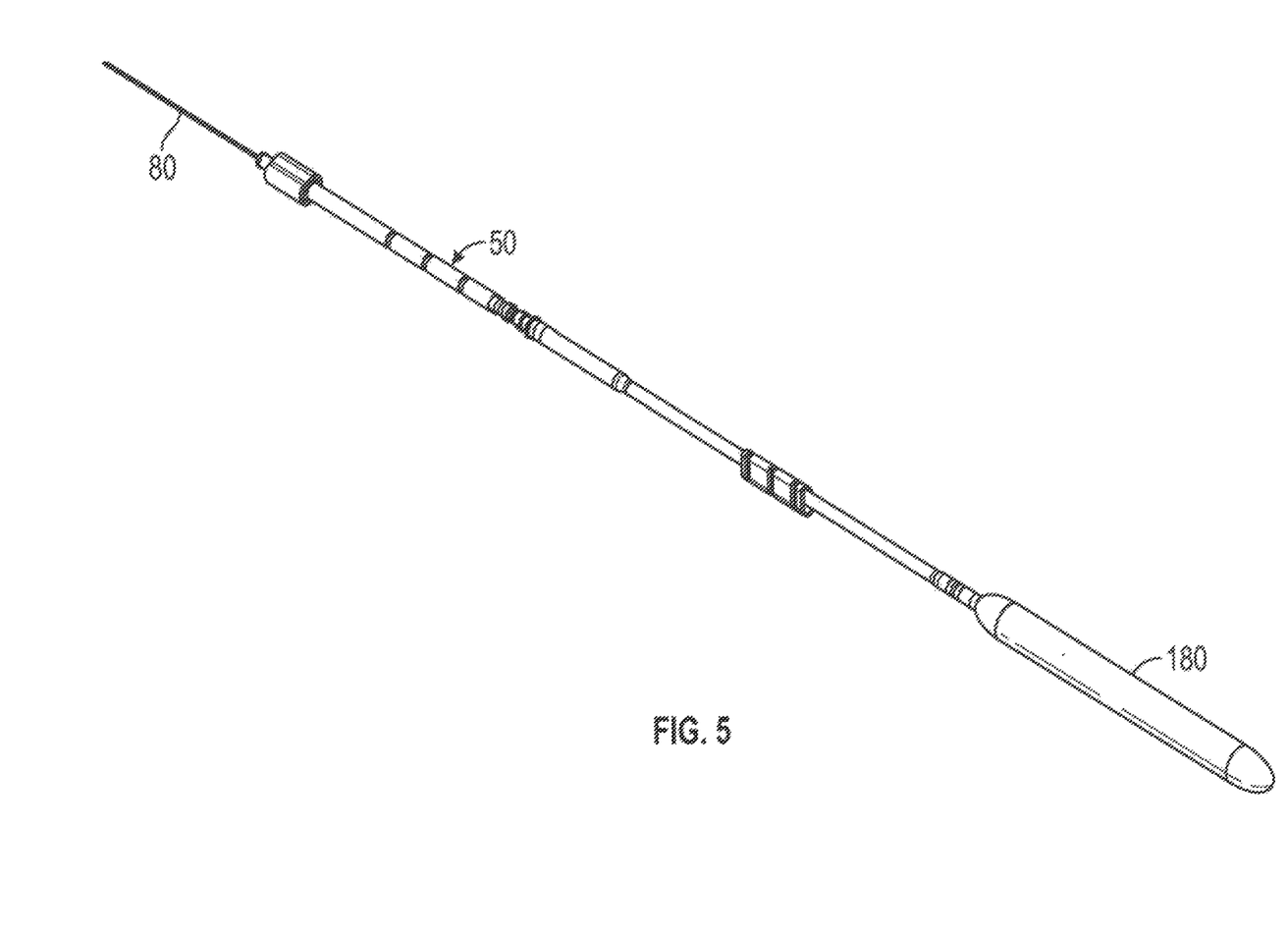
FIG. 5 schematically shows introducer assembly 50 coupled to blood pump 180 during implantation of the blood pump 180 into a patient.
Figure 10:
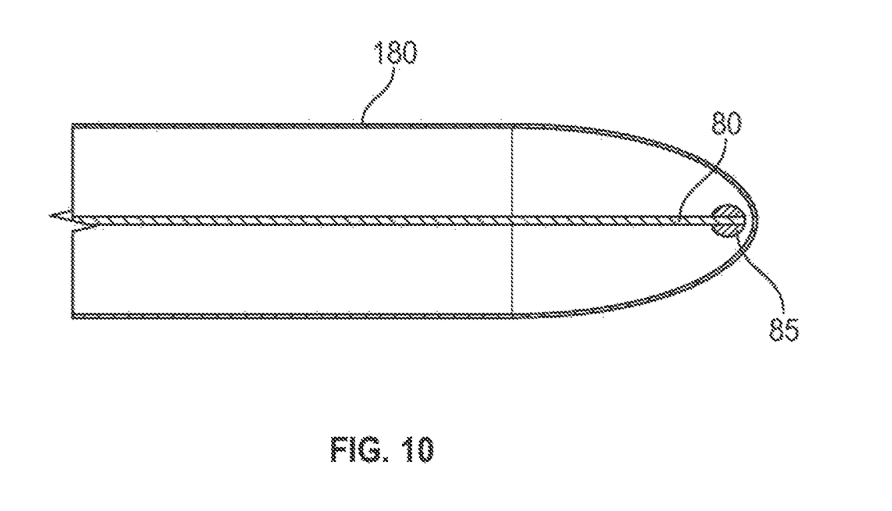
FIG. 10 is an expanded cross-sectional view of a distal portion of blood pump 180 in which a blunt tip 85 of guidewire 80 is advanced to the distal tip of the blood pump during delivery.
Figure 11:
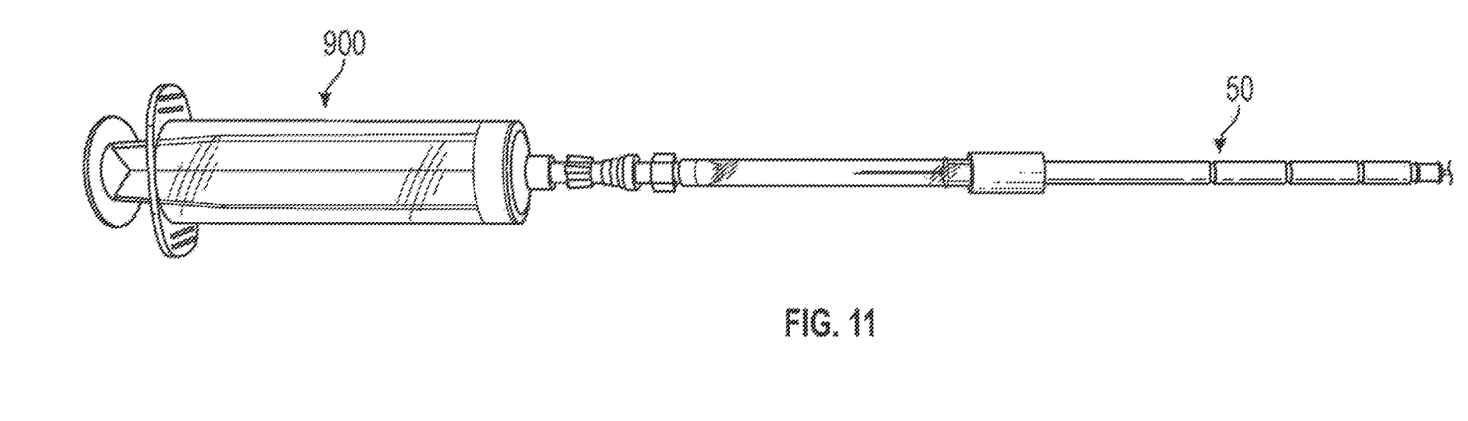
FIG. 11 shows an assembly of introducer assembly 50 in combination with a vacuum device 900 (i.e., syringe) during implantation of a blood pump.

During installation of the blood pump 180, guidewire 80 is inserted into the blood pump 180 so the wire's blunt distal end contacts 85 the distal inside tip of the pump (FIG. 10). Thus the guidewire 80 is within the central lumen of the blood pump 180 during insertion as opposed to being in an auxiliary lumen or on the outside surface of the balloon. The distal end of the introducer shaft is then mechanically attached to the proximal end of the pump as shown in FIG. 5. Collet mechanism 75 and associated locking component 90 are used to lock the guidewire 80 into place. A vacuum device 900 (i.e., a syringe as in FIG. 11) is then used to pull a vacuum on the blood pump (not shown) minimizing its size. Once the blood pump is placed, the vacuum is released, the guidewire 80 is extracted and the shaft is removed.

In embodiments, the access port assembly 800 may be removed during implantation of the blood pump 180. As such, the inner diameter of the port may be sized large enough such that it can accommodate the AID 150 and the introducer assembly 50. For example, once the blood pump 180 is placed within the artery, the access port assembly 800 may be detached and slid away from the patient over the introducer assembly 50 and guidewire 80. In embodiments, the inner diameter of the access port is greater than about 5, 6, 7, 8, 9, 10, 11, 12, 13, 14 or 15 mm. In one embodiment, the inner diameter of the access port is equal to or greater than about 7 or 8 mm.

To facilitate placement and detection of the blood pump 180 during installation, the guidewire 80, or portion thereof, may include a radiopaque material. For example, blunt end 85 may be composed of or otherwise include a radiopaque material. Alternatively, the blood pump 180, or portion thereof, may include a radiopaque material. In another embodiment, both the guidewire 80, or portion thereof, and the blood pump 180, or portion thereof include a radiopaque material.

Figure 12:
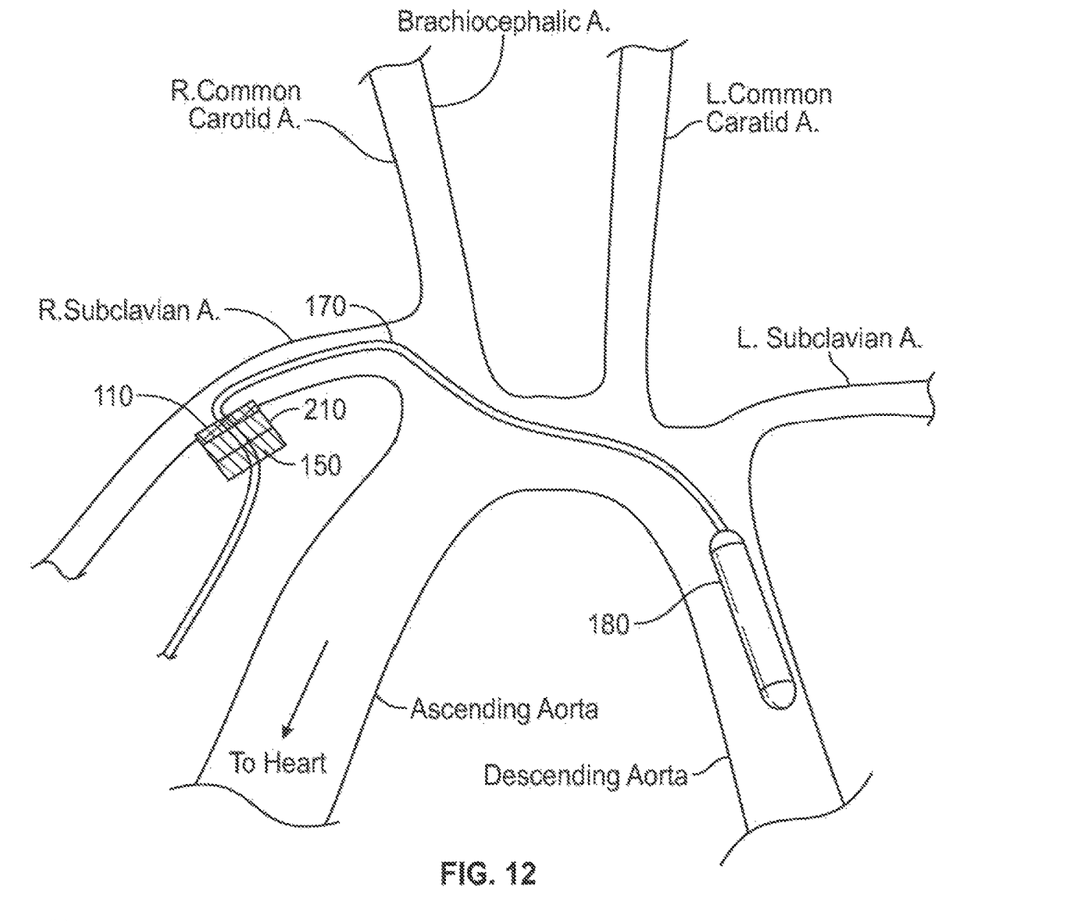
FIG. 12 schematically shows blood pump 180 positioned in the proximal descending aorta, with the pump's inflation catheter entering the vasculature at the right subclavian artery through AID 150.

FIG. 12 shows (schematically) the graft 110 in position on the right subclavian artery. This position is advantageous because it allows easy surgical access and a relatively short distance to the descending aorta. FIG. 12 also shows the graft secured to AID 150 by a suture 210. Other suitable positions for the interface include either common carotid artery, the brachiocephalic artery, the left subclavian artery, the descending aorta, and the abdominal aorta. Downstream branches of the aorta may also be used, such as the external iliac and femoral arteries.

Figure 13:
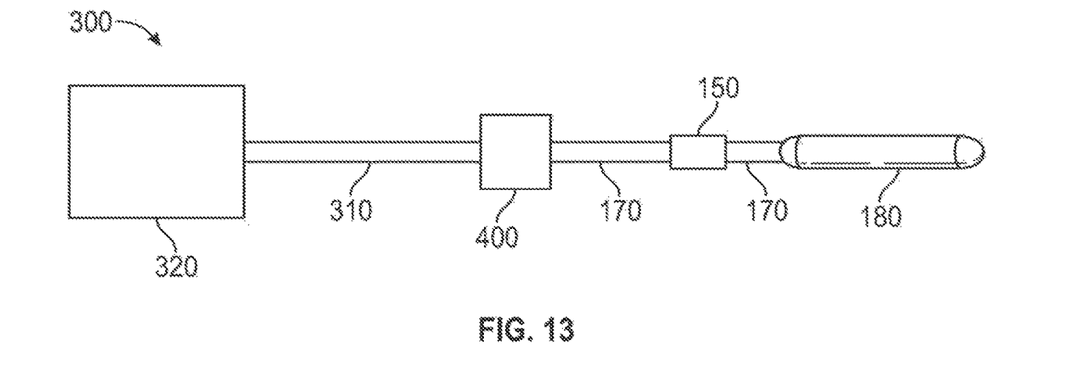
FIG. 13 schematically shows a CAD including blood pump 180, internal drive line 170, AID 150, SID 400, external drive line 310, and external driver 320.

Referring now to FIG. 13, in embodiments a CAD or iVAS comprises pump 180, internal drive line 170, AID 150, SID 400, external drive line 310, and external driver 320.

In embodiments, blood pump 180 is sized and shaped to dangle inside a patient's aorta and may optionally include a radiopaque material. In certain embodiments, the wall of the pump comprises moisture resistant material, or may be entirely moisture resistant, to keep the air inside the pump as dry as possible. One possible moisture resistant material for the pump comprises polyurethane. In certain embodiments, the one or more polyurethane polymers are modified to include surface silicone end groups.

At its proximal end, the pump 180 is connected to the distal end of the drive line 170. An AID 150 is sized and shaped to pass the drive line 170 through an arterial wall.

SID 400 connects the proximal end of the internal drive line 170 to the distal end of the external drive line 310. The proximal end of the external drive line 310 is connected to the driver 320.

The pump 180, the internal drive line 170, the SID 400, the external drive line 170, and the driver 320 can be charged with a pumping medium. In certain embodiments, the pumping medium comprises a fluid. A preferred pumping medium is air. In certain embodiments, pump 180, the internal drive line 170, the SID 400, the external drive line 310, and the driver 320 define a closed fluid system. In certain embodiments, pump 180, the internal drive line 170, the SID 400, the external drive line 310, and the driver 320 comprise an open system, wherein the bolus of air inside the system can be exchanged with the ambient environment.

As those skilled in the art will appreciate, pump 180 may have various sizes depending on the anatomy of the patient. In certain embodiments, pump 180 will typically have an inflated volume of about 40 to 60 cubic centimeters when inflated to 10 to 20 mmHg above the maximum systolic pressure.

In certain embodiments, sensors are connected to one or more communication interfaces that, like the pneumatic drive line 170, pass through the AID 150 and graft 110 and connect to SID 400. In certain embodiments, these one or more communication interfaces provide data to a controller.

In certain embodiments, one or more sensors transmit data, by wire or wirelessly, to Applicants' SID 400. Examples of sensors include, without limitation, electrical leads to measure an electrocardiogram, sensors to detect body temperature, sensors to detect blood analytes (such as blood gases), sensors to detect intra-arterial pressure directly or indirectly, and/or sensors to measure humidity within pump 180. Indirect sensors include, for example and without limitation, a microphone to monitor heart sounds.

In certain embodiments, a controller 530 is disposed in SID 400. In certain embodiments, a controller 530 is integral with external driver 320.

In certain embodiments, signals from one or more sensors are used by controller 530 to monitor the cardiac cycle and, thereby, the counterpulsation cycle. In certain embodiments, combinations of signals from one or more sensors are used by controller 530 to monitor the cardiac cycle.

In certain embodiments, sensors are used to determine the state of the air inside the system. In certain embodiments, air pressure is measured to determine whether the pump is properly inflating, or if there is a leak in the system. In certain embodiments, data from the air pressure sensor is communicated to controller 530.

In certain embodiments, sensors for arterial blood pressure at the pump 180 and/or at the AID 150 are in communication with controller 530. In certain embodiments, these sensors communicate a detected arterial blood pressure to the controller 530, either by wire or wirelessly.

Referring now to FIG. 7A, SID 400 comprises a SID base 500 and a SID cap 600. SID base 500 and SID cap 600 are coupled so as to create an air-tight conduit between the internal drive line 170 and external drive line 310. In this way, drive line 170, SID 400, and drive line 310, can be part of a closed fluid system. In certain embodiments, an air-tight seal is formed using gaskets and other sealing systems.

Referring now to FIGS. 7A and 7B, when implanted skin interface device 400 includes a SID base 500, comprising a subcutaneous portion 430 internal to the patient, in combination a supracutaneous portion 420. SID cap 600 is attached to the supracutaneous portion 420 of SID base 500. Those skilled in the art will appreciate that it is possible to implant SID 400 in a variety of different locations on the patient, for example abdominally or thoracically.

Referring now to FIG. 7A, SID 400 wirelessly provides electrical energy from SID cap 600 to SID base 500, and also wirelessly and bi-directionally passes electrical signals, i.e., data, between SID cap 600 and SID base 500. In order to optimize the transmission of power from SID cap 600 to SID base 500, and at the same time optimize the transmission of data between SID cap 600 and SID base 500, Applicants have "decoupled" the transmission of power from the transmission of data. The transmission of power from SID cap 600 to SID base 500 is done by induction.

While the preferred embodiments of the present invention have been illustrated in detail, it should be apparent that modifications and adaptations to those embodiments may occur to one skilled in the art without departing from the scope of the present invention as set forth herein. The invention is illustrated in part by the following example, provided however, that the invention is solely defined by the appended claims.

What is claimed is:

1. An introducer assembly for introducing a blood pump comprising:
    a shaft elongated along a longitudinal axis, the shaft having a distal end, a proximal end, a lumen extending along the longitudinal axis from the distal end to the proximal end, and a collet mechanism disposed at the proximal end for receiving a guidewire; and
    a locking component having a distal end and a proximal end, the locking component adapted such that the distal end of the locking component reversibly couples to the proximal end of the shaft,
    wherein the locking component has a locked configuration and an unlocked configuration, and
    wherein when in the locked configuration, a gripping force is created between the collet mechanism and the guidewire.

2. The assembly of claim 1, wherein the distal end of the shaft is fluidly coupled with a drive line of a blood pump device.

3. The assembly of claim 2, wherein a hose barb is disposed at the distal end of the shaft.

4. The assembly of claim 2, wherein the distal end of the shaft is connected to the drive line via an intermediate length of tubing.

5. The assembly of claim 4, wherein the shaft and driveline are easily connectable via manual manipulation by a practitioner without the assistance of a tool.

6. The assembly of claim 2, wherein the blood pump device comprises an elongated inflatable balloon having a proximal end and a distal end, wherein the proximal end of the balloon is coupled to the drive line.

7. The assembly of claim 6, wherein the balloon is sized to displace 50 cc of fluid when inflated upon implantation into a blood vessel.

8. The assembly of claim 6, wherein the blood pump device comprises a radiopaque marker.

9. The assembly of claim 8, wherein the radiopaque marker is disposed on the drive line adjacent the proximal end of the balloon.

10. The assembly of claim 2, wherein the guidewire comprises a rounded surface at a distal tip of the guidewire configured to contact the distal end of the balloon.

11. The assembly of claim 10, wherein the rounded surface comprises a sphere.

12. The assembly of claim 10, wherein the guidewire or a portion thereof is composed of a radiopaque material.

13. The assembly of claim 12, wherein the rounded surface comprises radiopaque material.

14. The assembly of claim 1, wherein the locking component and the shaft are threadably attached.

15. The assembly of claim 14, wherein the locking component comprises female threads and the shaft comprised male threads.

16. The assembly of claim 14, wherein the locking component comprises male threads and the shaft comprises female threads.

17. The assembly of claim 1, wherein the proximal end of the shaft is adapted to form a fluid tight seal with the locking component.

18. The assembly of claim 17, wherein proximal end of the shaft comprises an o-ring to provide the fluid tight seal.

19. The assembly of claim 1, wherein the proximal end of the locking component is adapted to fluidly couple with a pneumatic drive line.

20. The assembly of claim 19, wherein a hose barb is disposed at the proximal end of the locking component.

* * * * *